US012599653B2

(12) United States Patent
Hong et al.

(10) Patent No.: US 12,599,653 B2
(45) Date of Patent: Apr. 14, 2026

(54) THROMBOLYTIC AGENTS FOR INTRAVASCULAR CLOTS

(71) Applicant: JINIS CO., LTD., Wanju-gun (KR)

(72) Inventors: Seong Tshool Hong, Jeonju-si (KR); Hyeon Jin Kim, Wanju-gun (KR); Mdmehedi Hassan, Jeonju-si (KR)

(73) Assignee: JINIS CO., LTD., Wanju-gun (KR)

( * ) Notice: Subject to any disclaimer, the term of this patent is extended or adjusted under 35 U.S.C. 154(b) by 745 days.

(21) Appl. No.: 17/770,795

(22) PCT Filed: Oct. 19, 2020

(86) PCT No.: PCT/KR2020/014217
§ 371 (c)(1),
(2) Date: Apr. 21, 2022

(87) PCT Pub. No.: WO2021/080262
PCT Pub. Date: Apr. 29, 2021

(65) Prior Publication Data
US 2022/0362355 A1 Nov. 17, 2022

(30) Foreign Application Priority Data

Oct. 22, 2019 (KR) ........................ 10-2019-0131585

(51) Int. Cl.
| | |
|---|---|
| *C12N 9/50* | (2006.01) |
| *A61K 38/00* | (2006.01) |
| *A61K 38/48* | (2006.01) |
| *A61P 7/02* | (2006.01) |

(52) U.S. Cl.
CPC .......... *A61K 38/484* (2013.01); *A61K 38/482* (2013.01); *A61P 7/02* (2018.01); *C12N 9/50* (2013.01); *C12Y 304/21073* (2013.01)

(58) Field of Classification Search
CPC ....... A61K 38/484; A61K 38/482; A61P 7/02; C12N 9/50; C12Y 304/21073; C12Y 304/21; C12Y 304/21068
See application file for complete search history.

(56) References Cited

U.S. PATENT DOCUMENTS

| | | | |
|---|---|---|---|
| 3,855,065 | A | 12/1974 | Feldman |
| 4,259,447 | A | 3/1981 | Haefeli |
| 4,766,075 | A | 8/1988 | Goeddel et al. |
| 4,851,345 | A | 7/1989 | Hayashi et al. |
| 5,011,686 | A | 4/1991 | Pang |
| 5,055,295 | A | 10/1991 | Welzel et al. |
| 5,185,259 | A | 2/1993 | Goeddel et al. |
| 5,587,159 | A | 12/1996 | Goeddel et al. |
| 5,869,314 | A | 2/1999 | Goeddel et al. |
| 6,004,794 | A | 12/1999 | Karran et al. |
| 6,274,335 | B1 | 8/2001 | Goeddel et al. |
| 6,759,042 | B2 | 7/2004 | Higazi |
| 6,812,339 | B1 | 11/2004 | Venter et al. |
| 7,105,327 | B1 | 9/2006 | Kuppusamy et al. |
| 7,452,708 | B2 | 11/2008 | Darrow et al. |
| 2003/0157685 | A1 | 8/2003 | Zervos |
| 2004/0171105 | A1 | 9/2004 | Du et al. |
| 2006/0264363 | A1 | 11/2006 | Doi et al. |
| 2007/0065897 | A1 | 3/2007 | Darrow et al. |
| 2020/0103419 | A1 | 4/2020 | Arboleda-Velasquez |

FOREIGN PATENT DOCUMENTS

| | | | |
|---|---|---|---|
| EP | 1669089 | A1 | 6/2006 |
| JP | H10117789 | A | 5/1998 |
| JP | 2003517269 | A | 5/2003 |
| JP | 2005154399 | A | 6/2005 |
| KR | 20010043127 | A | 5/2001 |
| KR | 20150129847 | A | 11/2015 |
| KR | 20180081451 | A | 7/2018 |
| RU | 2745847 | C2 | 4/2021 |
| WO | 1998050406 | A1 | 11/1998 |

(Continued)

OTHER PUBLICATIONS

Zurawa-Janicka et al. "Structural insights into the activation mechanisms of human HtrA serine proteases," Archives of Biochemistry and Biophysics 621: 6-23 (2017) (Year: 2017).*

Human HtrA serine peptidase 1 (UniProtKB Accession No. A0A3B3IU24, accessed Apr. 10, 2025 at URL: uniprot.org/uniprot/A0A3B3IU24, pp. 1-3 (Year: 2025).*

Drumm et al, Genetic Variation and Clinical Heterogeneity in Cystic Fibrosis, Annu. Rev. Pathol. Mech. Dis., 2012, 7, pp. 267-282 (Year: 2012).*

Yampolsky et al, The Exchangeability of Amino Acids in Proteins, Genetics, 2005, 170, pp. 1459-1472. (Year: 2005).*

UniProtKB Accession No. Q92743, accessed Jul. 29, 2025 at URL: uniprot.org/uniprotkb/Q92743, pp. 1-10 (Year: 2025).*

UniProtKB Accession No. A0A384MDW9, accessed Jul. 29, 2025 at URL: uniprot.org/uniprotkb/ A0A384MDW9, pp. 1-3 (Year: 2025).*

(Continued)

*Primary Examiner* — Julie Ha
*Assistant Examiner* — Kristina M Hellman
(74) *Attorney, Agent, or Firm* — NKL Law; Jae Youn Kim

(57) ABSTRACT

Provided is a thrombolytic agent for 'intravascular thrombus', and more particularly, to a thrombolytic agent having a thrombo-recognition domain and a thrombolytic domain. It also relates to a polypeptide for thrombolysis of an intravascular thrombus, a gene for that polypeptide, and a pharmaceutical composition containing the same. The polypeptide that recognizes 'intravascular thrombus' and dissolves thrombus of the present invention is characterized in that it consists of a thrombolytic domain comprising the amino acid sequence set forth in SEQ ID NO: 1 or SEQ ID NO: 2 and a thrombo-recognition domain comprising the amino acid sequence set forth in SEQ ID NO: 3 or SEQ ID NO: 4. According to the present invention, the polypeptide for dissolving thrombus by recognizing 'intravascular thrombus' dissolves thrombus in the blood of a mammal without serious bleeding side effects has a preventive and therapeutic effect on thrombosis, thus preventing thrombosis and related diseases.

1 Claim, 9 Drawing Sheets

Specification includes a Sequence Listing.

(56)                    References Cited

FOREIGN PATENT DOCUMENTS

| | | |
|---|---|---|
| WO | 99/55885 A2 | 11/1999 |
| WO | 2014151734 A1 | 9/2014 |
| WO | 2018183213 A1 | 10/2018 |

OTHER PUBLICATIONS

Kujovich, "Factor V Leiden thrombophilia," Genetics Med 13:1-16 (2011) (Year: 2011).*

Mackman, "Triggers, targets and treatments for thrombosis," Nat 451:914-918 (2008) (Year: 2008).*

"Synthetic construct DNA, clone: pFN21AB5246, Homo sapiens HTRA1 gene for HtrA serinepeptidase 1, without stop codon, in Flexi system" GenBank database sequence No. AB590567.1, posted Jul. 25, 2016.

"Synthetic construct Homo sapiens clone ccsbBroadEn_08088 HTRA2 gene, encodescomplete protein" GenBank database sequence No. KJ898694.1, posted on Mar. 19, 2015.

Yang X.J.et al., "High-level expression and deletion mutagenesis of human tryptophan hydroxylase", Proc Natl Acad Sci USA, 1994, v.91, n.14, p. 6659-6663.

Frankel A.E. et al., "Characterization of diphtheria fusion proteins targeted to the human interleukin-3 receptor", Protein Eng., 2000, v.13, n.8, p. 575-581.

Pakula A.A. et al., "Genetic analysis of protein stability and function". Annu. Rev. Genet. 1989, v.23, p. 289-310.

Tokuriki N. et al., "Stability effects of mutations and protein evolvability", Curr. Opin. Struct. Biol., 2009, v.19, n.5, p. 596-604.

Muller S. et al., "Spliceosomal peptide P140 for immunotherapy of systemic lupus erythematosus" results of an early phase II clinical trial, Arthritis & Rheumatism: Official Journal of the American College of Rheumatology, 2008, v. 58, n. 12, p. 3873-3883.

Mola J.R. et al., "Non-viral nanovectors for gene delivery: factors that govern successful therapeutics", Expert Opin. Drug Deliv., 2010, v. 7, is. 6, p. 721-735.

Khan K. H., "Gene expression in Mammalian cells and its applications", Advanced Pharmaceutical Bulletin, 2013, v. 3, n. 2, p. 257-263.

Serine Protease HtrA1 Is Developmentally Regulated in Trophoblast and Uterine Decidual Cells During Placental Formation in the Mouse, Develpmental Dynamincs, by Guiwing Nie, et al., 233: 1102-1109, 2005.

NCBI, GenBack accession No. NP_002766.1, serine protease HTRA1 precursor [*Homo sapiens*] Sep. 3, 2019.

NCBI, GenBank accession No. NP_037379.1, serine protease HTRA2, mitochondrial isoform 1 preproprotein [*Homo sapiens*] Oct. 7, 2019.

NCBI, GenBank accession No. NM_002775.5, *Homo sapiens* HtrA serine peptidase 1 (HTRA1), mRNA, Sep. 3, 2019.

NCBI, GenBank accession No. NM_013247.4, *Homo sapiens* HtrA serine peptidase 2 (HTRA2), transcript variant 1, MRNA, Oct. 8, 2019.

Chu, Q. et al., "HtrA1 Proteolysis of ApoE in vitro is Allele Selective", JACS, 138(30), Total p. 15, Aug. 3, 2016.

* cited by examiner

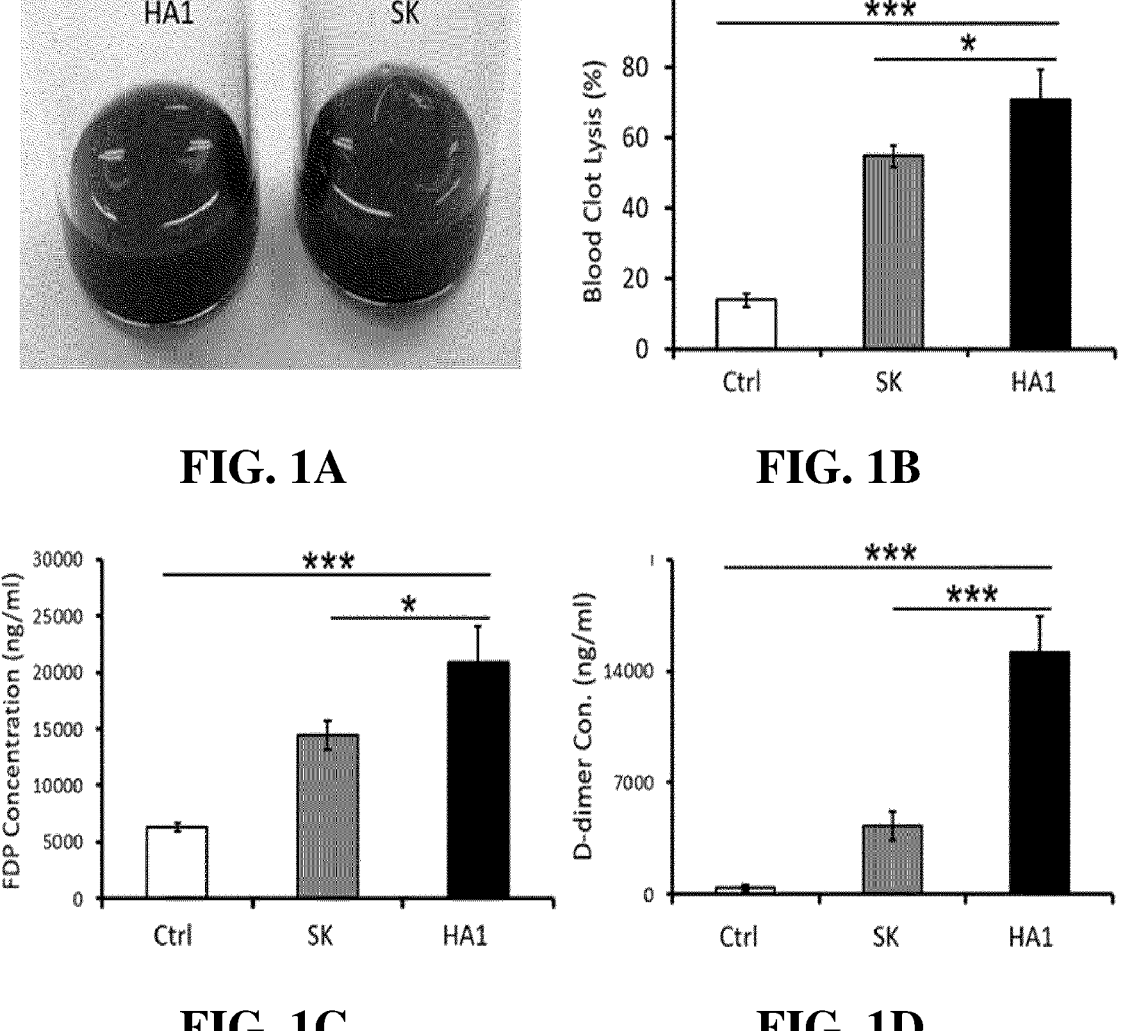
FIG. 1A                                FIG. 1B
FIG. 1C                                FIG. 1D

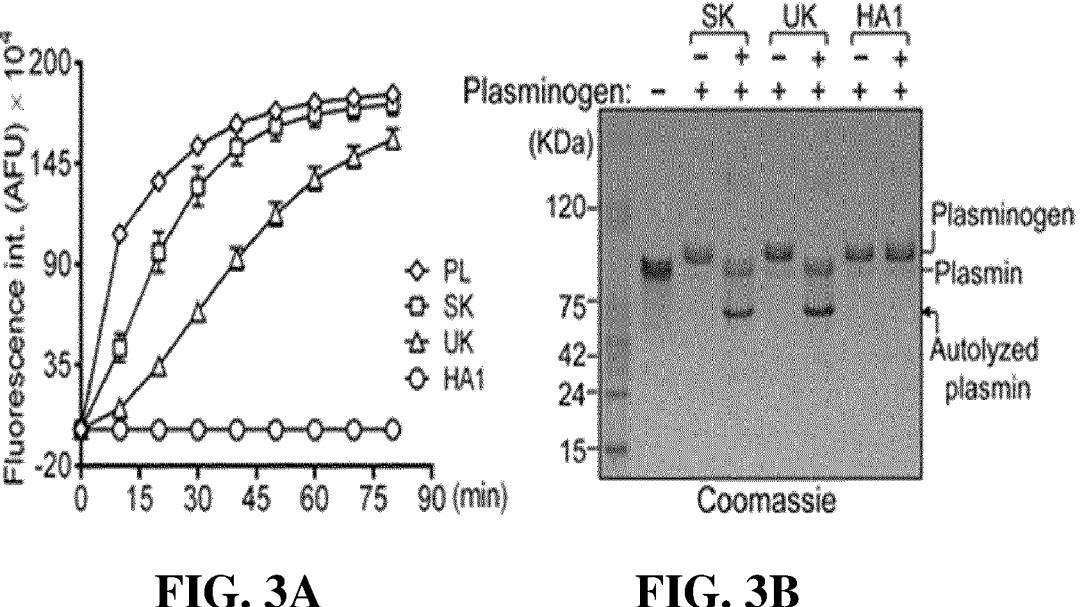
FIG. 3A          FIG. 3B
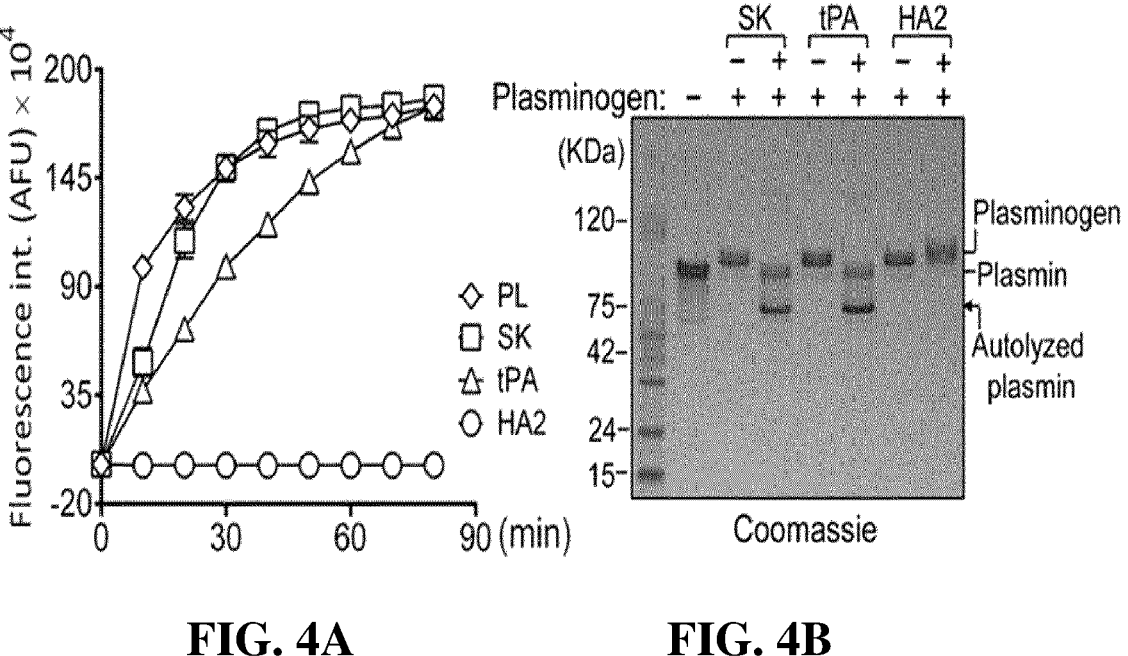
FIG. 4A          FIG. 4B

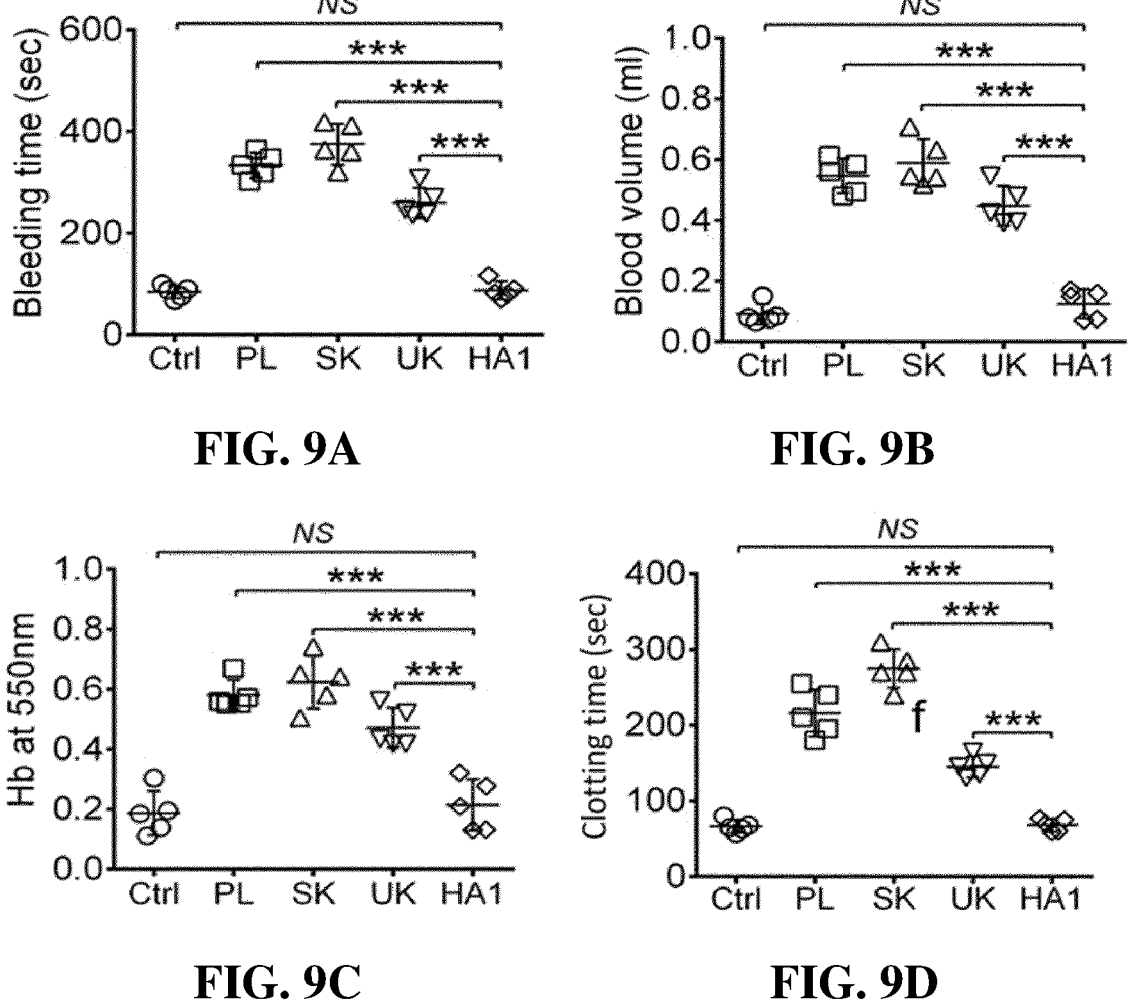
FIG. 9A                  FIG. 9B
FIG. 9C                  FIG. 9D

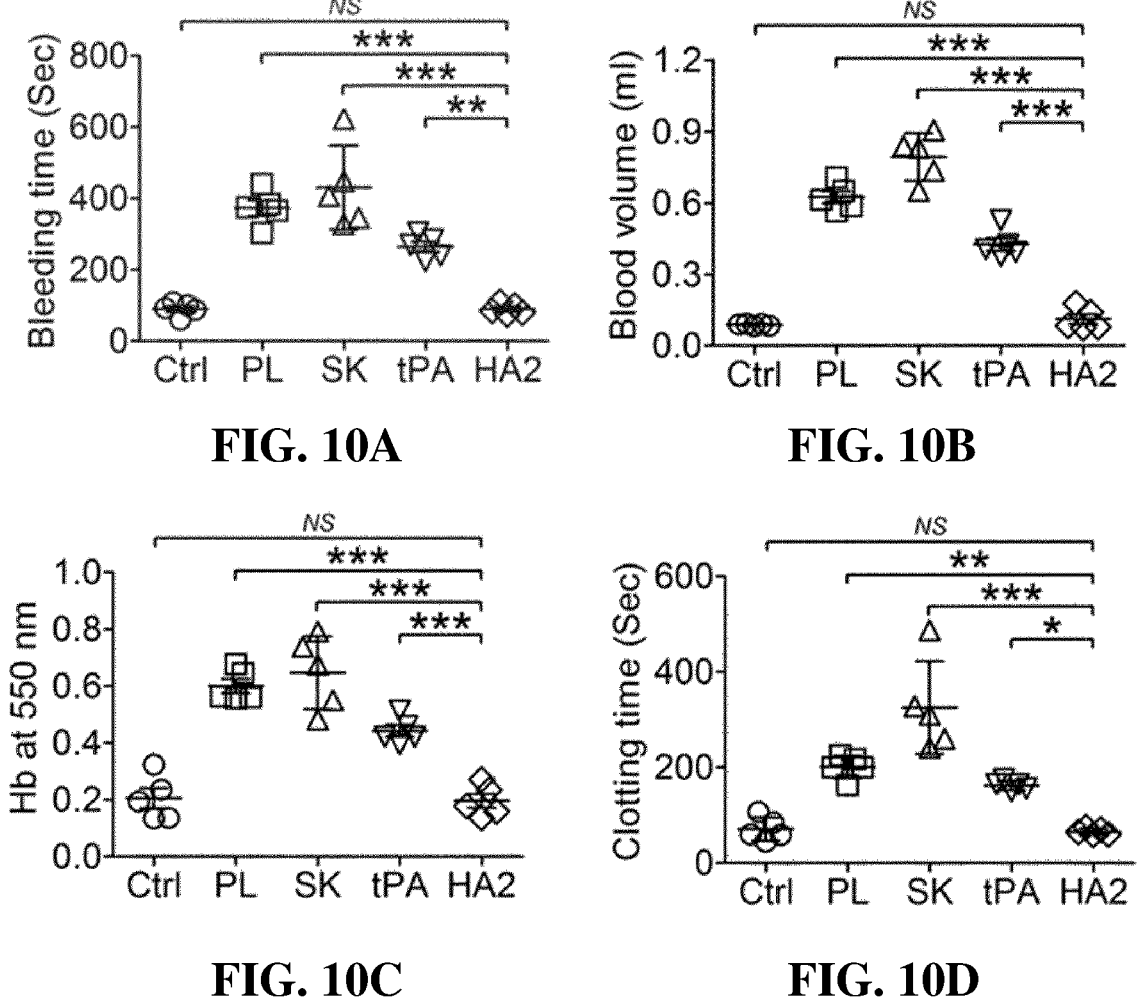
FIG. 10A          FIG. 10B
FIG. 10C          FIG. 10D

THROMBOLYTIC AGENTS FOR INTRAVASCULAR CLOTS

INCORPORATION OF SEQUENCE LISTING

This application contains a sequence listing in Computer Readable Form (CRF). The CRF file containing the sequence listing entitled "10-PK3805353-SeqListing.txt", which was created and modified on Apr. 21, 2022, and is 16,418 bytes in size. The information in the sequence listing is incorporated herein by reference in entirety.

TECHNICAL FIELD

The present invention relates to a thrombolytic agent for 'intravascular thrombus', and more particularly, to a thrombolytic agent having a thrombo-recognition domain and a thrombolytic domain. The present invention also relates to a polypeptide for thrombolysis of an intravascular thrombus, a gene for that polypeptide, and a pharmaceutical composition containing the same.

BACKGROUND ART

When a blood vessel tissue is injured, blood flows out of the blood vessel. To prevent bleeding, a blood clot forms in the blood vessel tissue around the wound. This tissue thrombus, which is confined to the wound site and prevents bleeding, is a normal wound healing process and is an essential process for the survival of animals including humans. On the other hand, an abnormal blood clot within a blood vessel is referred as 'intravascular thrombus'. If the blood clot is not removed, blood flow is blocked, causing the occurrence of thrombosis. When blood flow is blocked, it causes fatal thrombosis diseases such as stroke, pulmonary infarction, and myocardial infarction that cause tissue necrosis due to hypoxia. Therefore, if thrombosis occurs, immediate treatment is urgently needed.

Various therapeutic agents have been developed to treat thrombosis, which is a very serious disease and has a high incidence rate. Thrombolytics are direct therapeutic agents that dissolve thrombus, such as tissue-type plasminogen activator (tPA) (U.S. Pat. Nos. 4,766,075, 5,185,259, 5,587,159, 5,869,314, 6,274,335), urokinase (U.S. Pat. Nos. 4,259,447, 4,851,345, 5,055,295, 6,759,042), and streptokinase (U.S. Pat. Nos. 3,855,065, 5,011,686), U.S. Pat. No. 7,105,327). These thrombolytic agents, i.e., tPA (alteplase, reteplase), urokinase, and streptokinase, all bind to plasminogen in the body and activate it into plasmin, the activated enzyme that breaks down the thrombus, resulting thrombolysis. However, the activated thrombolytic plasmin also degrades hemostatic blood clots that were formed to prevent bleeding from damaged blood vessels, causing severe bleeding from the wound site. This is because plasmin is a non-specific thrombolytic agent that does not have specificity for 'intravascular thrombus'. Because of the serious bleeding side effects of plasmin, the thrombolytic agents that produce plasmin, such as tPA, urokinase, and streptokinase, are all used only in limited cases.

Because of the fatal side effects of these thrombolytics, anticoagulants such as heparin, warfarin, davigatran, etc., or antiplatelets such as aspirin are used clinically instead of thrombolytic drugs for thrombotic patients. Anticoagulants and antiplatelet agents cannot dissolve clots that have already formed but prevent the additional clot formation in the blood vessels. Thus, they have no significant effect on the treatment of thrombosis although they do not cause fatal systemic bleeding, unlike plasmin-activating thrombolytics. In addition, anticoagulants and antiplatelet agents interfere with the formation of normal hemostatic blood clots and thus interfere with wound healing, resulting in serious bleeding from damaged vessels without wound healing.

Therefore, in order to treat thrombosis, there is an urgent need to develop a thrombolytic agent specific to 'intravascular thrombus' that accurately recognizes and decomposes only 'intravascular thrombus', but not hemostatic thrombus, and minimizes bleeding side effects without interfering with normal wound healing.

DISCLOSURE OF INVENTION

Technical Problem

The present inventors recognized that an ideal thrombosis treatment would be a thrombolytic agent specific for the 'intravascular thrombus' that dissolves 'intravascular thrombus' only without interfering with the normal blood clotting process and wound healing that occurs in vascular tissue. Efforts were made to develop a thrombolytic agent specific for the 'intravascular thrombus'. Therefore, one object of the present invention is to provide an innovative thrombolytic agent for 'intravascular thrombus' as a thrombosis treatment, which does not have any serious bleeding side effects such as fatal systemic bleeding due to its specific dissolution of 'intravascular thrombus' causing thrombosis.

Technical Solution

To achieve the above goal, the present invention provides a polypeptide having a thrombolytic domain comprising the amino acid sequence shown in SEQ ID NO: 1 or SEQ ID NO: 2 and a thrombo-recognition domain comprising the amino acid sequence shown in SEQ ID NO: 3 or SEQ ID NO: 4, thereby providing a polypeptide for the recognition and dissolution of 'intravascular thrombi'.

The present invention also provides a thrombolytic domain gene, characterized in that it has the nucleotide sequence shown in SEQ ID NO: 5 or SEQ ID NO: 6, which encodes a thrombolytic domain having the amino acid sequence shown in SEQ ID NO: 1 or SEQ ID NO: 2.

The present invention also provides a thrombo-recognition domain gene encoding a thrombo-recognition domain having an amino acid sequence shown in SEQ ID NO: 3 or SEQ ID NO: 4, characterized in that it has a nucleotide sequence shown in SEQ ID NO: 7 or SEQ ID NO: 8.

The present invention also provides a pharmaceutical composition for treating or preventing thrombosis and related diseases, characterized in that it contains a polypeptide or a gene encoding the same as an active ingredient by recognizing 'intravascular thrombus' and dissolving the 'intravascular thrombus'.

Benefits

According to the present invention, the polypeptide for dissolving thrombus by recognizing 'intravascular thrombus' dissolves thrombus in the blood of a mammal without serious bleeding side effects, thereby having preventive and therapeutic efficacy against thrombosis.

BRIEF DESCRIPTION OF THE DRAWINGS

FIGS. 1A-1D are results of confirming the thrombolytic ability after treatment of the thrombolytic enzyme SK or HtrA1 in the ex vivo thrombus according to Experimental Example 1 of the present invention (FIG. 1A; image in which the thrombus is dissolved (HA1) and undissolved thrombus mass (SK), FIG. 1B; thrombus solubility expressed in % before treatment, FIG. 1C; fibrin degradation products (FDP) from thrombotic dissolution, FIG. 1D; the amount of D-dimer from thrombotic dissolution (Ctrl: control, SK: streptokinase, HA1: Polypeptide HtrA1 that recognizes 'intravascular thrombus' and dissolves thrombus)).

FIGS. 3A and 3B are results of confirming the activity of plasminogen activation to plasmin of the 'intravascular thrombolytic' polypeptide HtrA1 according to Experimental Example 2 of the present invention (FIG. 3A; measurement of fluorescence intensity of a substrate dissolved by plasmin generated by plasminogen activation; FIG. 3B; SDS-PAGE image confirming the plasmin band generated by the activation of plasminogen (Ctrl: control, PL: plasmin, SK: streptokinase, UK: urokinase, HA1: Polypeptide HtrA1 that recognizes 'intravascular thrombus' and dissolves thrombus)).

FIGS. 4A and 4B are results of confirming the activity of plasminogen activation to plasmin of the 'intravascular thrombolytic' polypeptide HtrA1 according to Experimental Example 2 of the present invention (FIG. 4A; measurement of fluorescence intensity of a substrate dissolved by plasmin generated by plasminogen activation; FIG. 4B; SDS-PAGE image confirming the plasmin band generated by the activation of plasminogen (Ctrl: control, PL: plasmin, SK: streptokinase, UK: urokinase, HA2: Polypeptide HtrA2 that recognizes 'intravascular thrombus' and dissolves thrombus)).

FIGS. 9A-9D are bleeding test results confirming the effect of the 'intravascular thrombolytic' polypeptide HtrA1 of the present invention on wound healing using a wound animal model according to Example 3 of the present invention. (FIG. 9A; Measurement of bleeding time, FIG. 9B; Measurement of hemorrhage, FIG. 9C; Measurement of hemoglobin content in the bleeding fluid, FIG. 9D; Measurement of time taken to wound healing and blood clotting (Ctrl: control, PL: plasmin, SK: streptokinase, UK: urokinase, HA1: Polypeptide HtrA1 that recognizes 'intravascular thrombus' and dissolves thrombus)).

FIGS. 10A-10D are bleeding test results confirming the effect of the 'intravascular thrombolytic' polypeptide HtrA1 of the present invention on wound healing using a wound animal model according to Example 3 of the present invention. (FIG. 10A; Measurement of bleeding time, FIG. 10B; Measurement of hemorrhage, FIG. 10C; Measurement of hemoglobin content in the bleeding fluid, FIG. 10D; Measurement of time taken to wound healing and blood clotting (Ctrl: control, PL: plasmin, SK: streptokinase, UK: urokinase, HA2: Polypeptide HtrA2 that recognizes 'intravascular thrombus' and dissolves thrombus)).

DETAILED DESCRIPTION OF PREFERRED EMBODIMENTS

Figures 2A, 2B, 2C, 2D:
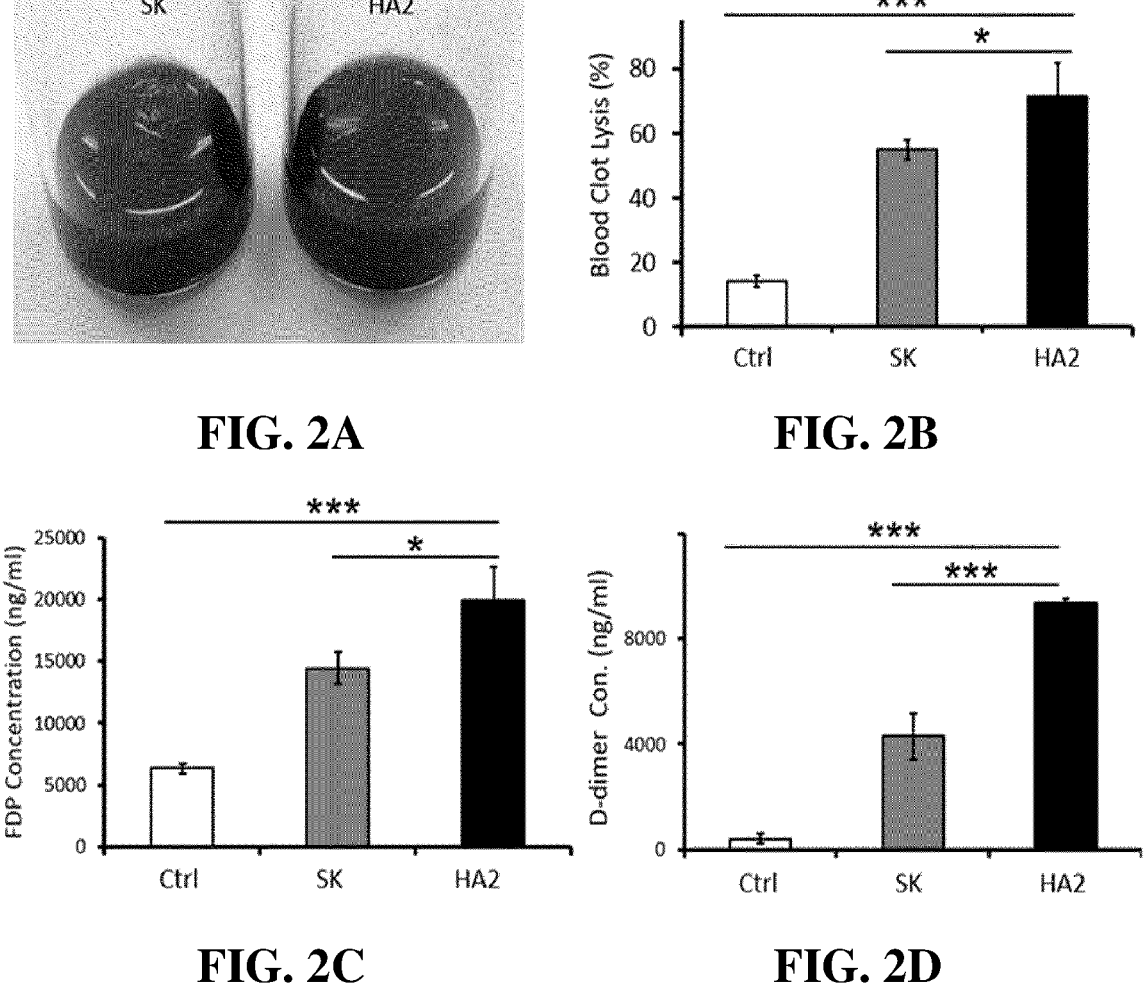
FIGS. 2A-2D are results of confirming the thrombolytic ability after treatment of the thrombolytic enzyme SK or HtrA2 in the ex vivo thrombus according to Experimental Example 1 of the present invention (FIG. 2A; image in which the thrombus is dissolved (HA2) and undissolved thrombus mass (SK), FIG. 2B; thrombus solubility expressed in % before treatment, FIG. 2C; fibrin degradation products (FDP) from thrombotic dissolution, d; the amount of D-dimer from thrombotic dissolution, (Ctrl: control, SK: streptokinase, HA2: Polypeptide HtrA2 that recognizes 'intravascular thrombus' and dissolves thrombus)).

Various agents have been developed to dissolve thrombus, an intravascular blood clot, but all the conventional thrombolytic agents have serious bleeding side effects, making it difficult to effectively treat thrombosis and related diseases. Furthermore, these treatments cannot effectively prevent thrombosis.

The present inventors focused on the fact that 'intravascular thrombus' is a kind of protein aggregate and that quality control proteins that degrade the aggregated proteins are essential for the survival of organisms. Through experiments were carried out to identify an endogenous proteinase having a domain that recognizes misfolded/aggregated protein and dissolves misfolded/aggregated protein in the body, and to confirm that this endogenous proteinase can dissolve the aggregated blood clots in blood vessels.

Accordingly, in the present invention, an extensive search was made for domains that recognize misfolded/aggregated proteins, for domains that dissolve misfolded/aggregated proteins, and for quality control proteins including these domains. As a result, it was confirmed that a polypeptide having a thrombo-recognition domain and a thrombolytic domain, can treat thrombosis without serious bleeding side effects by specifically recognizing 'intravascular thrombus' and specifically dissolving 'intravascular thrombus'.

In the present invention, a polypeptide that recognizes and dissolve 'intravascular thrombus' with an intravascular thrombo-recognition domain and a thrombolytic domain and dissolves a thrombus was confirmed that (1) it had excellent thrombolytic activity, (2) unlike conventional thrombolytic agents, there was no risk of bleeding due to plasmin production since it does not activate plasminogen into plasmin, (3) unlike conventional thrombolytic agents, it did not break down proteins which are important for wound healing, such as fibrinogen, c-fibronectin, and p-fibronectin, so that it does not interfere with wound healing, (4) it effectively treated thrombosis in an in vivo animal model, (5) it completely treated thromboembolism with a 100% survival rate in an in vivo animal model, unlike conventional thrombolytic agents, (6) there were no bleeding side effects as it did not interfere with blood clotting and wound healing of in vivo bleeding animal experiments, unlike conventional thrombolytic agents.

In one embodiment of the present invention, with the therapeutic efficacy in the mouse tail thrombosis model, it was confirmed that the polypeptide that recognizes and dissolves 'intravascular thrombus' of the present invention has cured thrombosis, unlike conventional thrombolytic agents.

In another embodiment of the present invention, it was confirmed that the polypeptide that recognizes and dissolves 'intravascular thrombus' of the present invention has cured fatal thromboembolism with a 100% survival rate while conventional thrombolytic agents failed to treat but resulted in deaths of mice.

In addition, in the mouse tail bleeding experiment, the polypeptide that recognizes and dissolves 'intravascular thrombus' of the present invention was confirmed to have a perfect wound healing efficacy without any bleeding side effects, being indistinguishable to the untreated control group in measures such as bleeding time at the wound site, amount of bleeding, amount of hemoglobin lost, and blood clotting time.

Accordingly, in one aspect, the present invention relates to a polypeptide that recognizes 'intravascular thrombus' and dissolves thrombus, wherein said polypeptide is characterized in that it consists of a thrombolytic domain comprising the amino acid sequence set forth in SEQ ID NO: 1 or SEQ ID NO: 2 and a thrombo-recognition domain comprising the amino acid sequence set forth in SEQ ID NO: 3 or SEQ ID NO: 4.

In the present invention, said polypeptide is composed of a thrombolytic domain comprising the amino acid sequence set forth in SEQ ID NO: 1 and a thrombo-recognition domain comprising the amino acid sequence set forth in SEQ ID NO: 3, or said polypeptide is composed of a thrombolytic domain comprising the amino acid sequence set forth in SEQ ID NO: 2 and a thrombo-recognition domain comprising the amino acid sequence set forth in SEQ ID NO: 4.

In the present invention, said polypeptide that recognizes the 'intravascular thrombus' and dissolves the thrombus is characterized in that it belongs to the serine protease which is a trypsin-like polypeptide, preferably High Temperature Requirement (Htr) family. More preferably, it is characterized in that it contains HtrA1 and HtrA2.

Said thrombolytic domain may be a domain having 50% or more, preferably 80% or more, more preferably 90% or more homology to the amino acid sequence of SEQ ID NO: 1 or SEQ ID NO: 2, wherein the thrombolytic domain is characterized as a domain conferring serine protease activity, including a peptide.

Said thrombo-recognition domain may be a domain having 50% or more, preferably 80% or more, more preferably 90% or more homology to the amino acid sequence of SEQ ID NO: 3 or SEQ ID NO: 4 and is characterized in that it has a topology structure composed of multiple combinations of beta-strand and alpha-helix. Thus, said thrombo-recognition domain may be a PDZ domain or a PDZ-like domain having a function of recognizing 'intravascular thrombus' and regulating the activity of a thrombolytic enzyme.

In another aspect, the present invention relates to a gene for the thrombolytic domain comprising the nucleotide sequence shown in SEQ ID NO: 5 or SEQ ID NO: 6, which encodes a thrombolytic domain having the amino acid sequence shown in SEQ ID NO: 1 or SEQ ID NO: 2.

Said thrombolytic domain gene is characterized in that it has 50% or more, preferably 80% or more, more preferably 90% or more homology to the nucleotide sequence of SEQ ID NO: 5 or SEQ ID NO: 6.

In another aspect, the present invention relates to a gene for the thrombo-recognition domain comprising the nucleotide sequence shown in SEQ ID NO: 3 or SEQ ID NO: 4, which encodes a thrombo-recognition having the amino acid sequence shown in SEQ ID NO: 7 or SEQ ID NO: 8.

Said thrombo-recognition domain gene is characterized in that it has 50% or more, preferably 80% or more, more preferably 90% or more homology to the nucleotide sequence of SEQ ID NO: 7 or SEQ ID NO: 8.

In another aspect, the present invention relates to a pharmaceutical composition for treating or preventing thrombosis and related diseases, characterized in that it contains a polypeptide or a gene encoding the same as an active ingredient for recognizing 'intravascular thrombus' and dissolving the thrombus.

The pharmaceutical composition of the present invention may include a pharmaceutically acceptable carrier commonly used in formulation, lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methylhydroxybenzoate, propylhydroxybenzoate, talc, magnesium stearate, mineral oil, etc. can be exemplified, The present invention is not limited thereto.

The pharmaceutical composition of the present invention may further include a lubricant, a wetting agent, a sweetening agent, a flavoring agent, an emulsifying agent, a suspending agent, a preservative, and the like, in addition to the above components. Suitable pharmaceutically acceptable carriers and agents are described in detail in Remington's Pharmaceutical Sciences (19th ed., 1995).

The pharmaceutical composition of the present invention may be administered orally or parenterally, preferably parenterally, and in the case of parenteral administration, intramuscular injection, intravenous injection, subcutaneous injection, intraperitoneal injection, topical administration, transdermal administration, etc.

A suitable dosage of the pharmaceutical composition of the present invention is variously prescribed depending on factors such as formulation method, administration method, age, weight, sex, pathological condition, food, administration time, administration route, excretion rate, and reaction sensitivity of the patient. Meanwhile, the preferred dosage of the pharmaceutical composition of the present invention is 0.0001-1000 µg per day.

The pharmaceutical composition of the present invention is prepared in unit dosage form by formulating using a pharmaceutically acceptable carrier and/or excipient according to a method that can be easily carried out by a person of ordinary skill in the art to which the present invention pertains. Or it can be prepared by introducing into a multidose container. In this case, the formulation may be in the form of a solution, suspension, or emulsion in oil or aqueous medium, or in the form of an extract, powder, granule, tablet, or capsule, and may additionally include a dispersant or stabilizer.

The pharmaceutical composition for treating or preventing thrombosis and related diseases, according to the present invention, has the effect of dissolving 'intravascular thrombus' while minimizing bleeding side effects when administered to a mammal.

In the present invention, the thrombosis and related diseases can be selected from the group that includes, but is not limited to, Thrombosis, Embolism, Thromboembolism, Arterial Thromboembolism, Venous Thromboembolism (VTE), cardiovascular disease, cerebrovascular disease, ischemic disease, etc. Specifically, it can be selected from the group that includes, but is not limited to, Deep Vein Thrombosis (DVT), Pulmonary Embolism (PE), ischemic stroke, stroke, cerebral hemorrhage, cerebral infarction, myocardial infarction, heart attack, and angina (unstable angina).

EXAMPLES

Hereinafter, the present invention will be described in more detail through specific examples. However, these Examples are only for describing the present invention in more detail, and the scope of the present invention is not limited by these Examples.

Experiment 1: Evaluation of Ex Vivo Thrombolytic Efficacy

Polypeptides HtrA1 and HtrA2 that recognize 'intravascular thrombus' and dissolve thrombus were prepared as recombinant proteins. The cDNA corresponding to 157-480 of the HtrA1 amino acid sequence (SEQ ID NO: 9) containing both the intravascular thrombo-recognition domain and the thrombolytic domain was used with a forward primer (5'-AATTCATATGCAAGGGCAGGAA-GATCCCA-3') (SEQ ID NO: 11) and a reverse primer (5'-TATCTCGAGCTATGGGTCAATTTCTTCGGG-3') (SEQ ID NO: 12) for amplification by PCR. For PCR conditions, after initial denaturation at 95° C. for 5 minutes, amplification (30 seconds at 95° C., 1 minute at 63° C., 2 minutes at 72° C.) was repeated 34 times, followed by 10 minutes at 72° C. The amplified product was subcloned into the NdeI/XhoI site of the expression vector pET28a+ (Novagen, USA). The obtained HtrA1 recombinant plasmid was electroporated into E.coli BL21 (DE3) pLysS (Stratagene, USA) and cultured with addition of IPTG for expression of HtrA1. The expressed culture medium was sonicated to make cell lysate, passed through econo-pac chromatography column (Bio-Rad), and then purified by PD-10 column (Amersham, US) to obtain recombinant protein HtrA1. In the case of HtrA2, the cDNA corresponding to 134-458 of the HtrA2 amino acid sequence (SEQ ID NO: 10) was used with a forward primer (5'-GTCCTCGCC- CATATGGCCGTCCCTAGCC-3') (SEQ ID NO: 13) and a reverse primer (5'-GGCTCTCGAGTCAT-TCTGTGACCTCAGGG-3') (SEQ ID NO: 14) was amplified by PCR. For PCR, after initial denaturation at 95° C. for 5 minutes, amplification (30 seconds at 95° C., 45 seconds at 65° C., 1 minute at 72° C.) was repeated 34 times, followed by 10 minutes at 72° C. After obtaining this, the recombinant protein HtrA2 was obtained by subcloning and expressing the pET28a+ expression vector (Novagen, USA) in the same manner as for HtrA1.

The thrombolytic activity of the recombinant proteins, HtrA1 and HtrA2, was confirmed with ex vivo thrombus. A thrombus was prepared using platelet-rich blood, and either 50 mM Tris-HCl control or each thrombolytic enzyme (2 mg/ml) was treated to the thrombus at 37° C. for 24 hours. After treatment, the weight of the thrombus was measured and expressed as a percentage before treatment. In addition, quantification was made for fibrin degradation products (FDP) and D-dimer generated by the degradation of fibrin polymer constituting the thrombus.

In FIGS. 1A-1D, the thrombolytic ability of HtrA1 (FIGS. 1A, 1B) and fibrin degradation ability (FIGS. 1C-1D) were the most excellent compared with the conventional thrombolytic enzymes. In FIGS. 2A-2D, HtrA2 also showed superior thrombolytic activity (FIGS. 2A-2B) and fibrin degrading ability (FIGS. 2C-2D) than conventional thrombolytic enzymes.

Experiment 2: Evaluation of Plasmin Generation (Thrombolytic Mechanism)

The current thrombolytic mechanism of thrombolytic agent is plasmin-dependent fibrinolysis by activating plasmininogen into plasmin. To confirm the mechanism of action compared to the conventional thrombolytic enzymes, each thrombolytic enzyme (0.1 mg/ml) was added to plasminogen (1.23 µM) and plasmin-specific fluorescent substrate, Boc-Glu-Lys-Lys-MCA (100 µM). After incubation, the activation of plasminogen to plasmin was confirmed by measuring the fluorescence intensity of the substrate dissolved by plasmin. Plasmin bands generated by the actual activation of plasminogen to plasmin were confirmed by SDS-PAGE after each enzyme (0.15 mg/ml) was added to plasminogen (5.14 µM).

Compared with the conventional thrombolytic enzyme, HtrA1 did not activate plasminogen (FIG. 3A), and thus there was no plasmin production (FIG. 3B). Similarly, HtrA2 also had no effect on plasminogen (FIG. 4A), and as a result, there was no plasmin production by HtrA2 (FIG. 4B).

Experiment 3: Evaluation of Thrombus Specificity

To evaluate the thrombus specificity of HtrA1, the fibrinolytic activities of components involved in the wound healing process were investigated. The fibrin clot obtained by reacting fibrinogen with thrombin was incubated with 50 mM Tris-HCl control or thrombolytic enzyme (2 mg/ml) at 37° C. for 24 hours. Dissolution of the fibrin clot was measured at a wavelength of 415 nm using a spectrophotometer. To see the activity of HtrA1 on fibrinogen, 5 µM fibrinogen was incubated with 50 mM Tris-HCl control or each thrombolytic enzyme (0.15 mg/ml) for 3 hours at 37° C. SDS-PAGE was carried out to confirm the fibrinolytic activity of HtrA1 on fibrinogen. To see the activity of HtrA1 on fibronectin, 1.5 µM fibronectin was incubated with 50 mM Tris-HCl control or each thrombolytic enzyme (0.15 mg/ml) for 3 hours at 37° C. and separated on a 4-12% SDS gel for immunostaining with cFN or anti-pFN antibody.

As shown in Table 1, HtrA1 and HtrA2 not only showed a statistically significant difference in absorbance when compared to the untreated control group, but also showed a statistically significant difference in absorbance for the conventional thrombolytic enzyme streptokinase. For fibrin clot dissolution, HtrA1 was the best, followed by HtrA2.

TABLE 1

| Groups | A415 |
| --- | --- |
| Control | $1.870 \pm 0.05$ |
| Streptokinase | $1.335 \pm 0.07^a$ |
| Urokinase | $1.047 \pm 0.06^a$ |
| HtrA1 | $1.055 \pm 0.10^{a,b}$ |
| HtrA2 | $1.002 \pm 0.09^{a,b}$ |

Figure 5A:
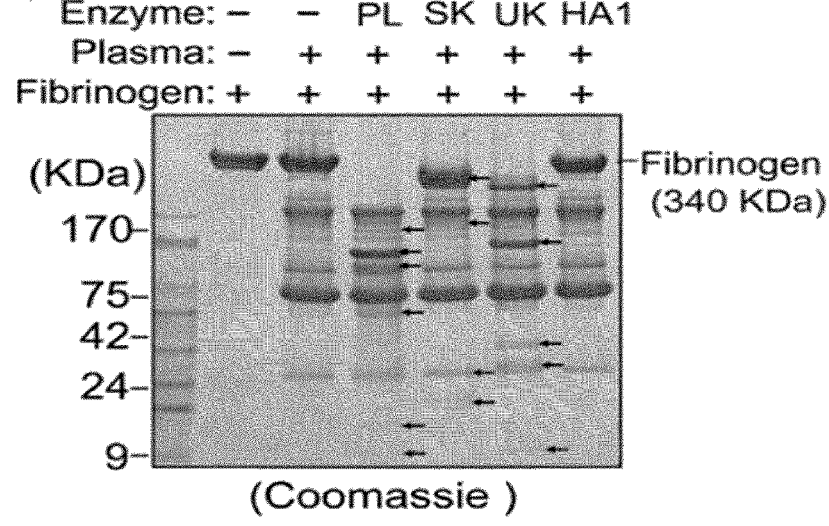
FIGS. 5A-5C are results of confirming the activity of the intravascular thrombolytic polypeptide of the present invention on the fibrinolysis components of the wound healing process in order to evaluate whether the thrombolytic polypeptide has thrombus specificity according to Experimental Example 3 of the present invention (FIG. 5A; SDS-PAGE image to confirm the degradation of fibrinogen into fibrin by treatment with each testing thrombolytic enzyme, FIG. 5B; Immuno-blot image to confirm the degradation of cellular fibronectin by treatment with each testing thrombolytic enzyme, FIG. 5C; Immuno-blot image to confirm the degradation of plasma fibronectin by treatment with each testing thrombolytic enzyme (Ctrl: control, PL: plasmin, SK: streptokinase, UK: urokinase, HA1: Polypeptide HtrA1 that recognizes 'intravascular thrombus' and dissolves thrombus)).
Figure 5B:
Figure 5C:
Figure 6:
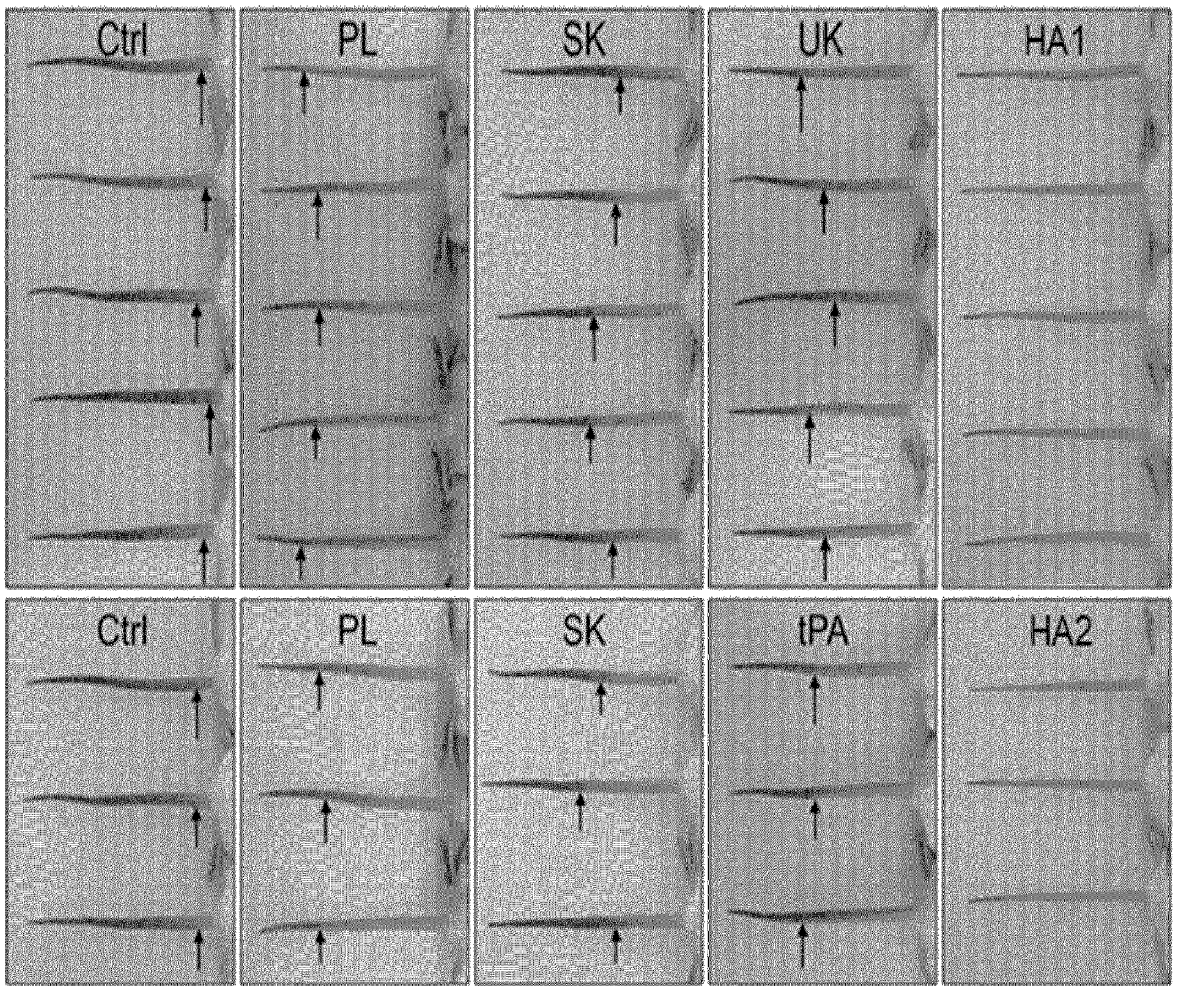
FIG. 6 is a thrombosis tail image result confirming the therapeutic efficacy of the 'intravascular thrombolytic' polypeptide of the present invention on thrombosis in tail thrombosis mice using an animal model according to Example 1 of the present invention (Ctrl: control, PL: Plasmin, SK: streptokinase, UK: urokinase, tPA: tissue plasminogen activator, HA1: Polypeptide HtrA1 that recognizes 'intravascular thrombus' and dissolves thrombus, HA2: Polypeptide HtrA2 that recognizes 'intravascular thrombus' and dissolves thrombus).

$^a$p < 0.05 significance difference from control group
$^b$p < 0.01 significance difference from Streptokinase group Unlike conventional thrombolytic enzymes, HtrA1 did not degrade fibrinogen, a critical component for hemostasis at the wound site (FIG. 5A). In addition, HtrA1 did degrade neither cellular fibronectin (FIG. 5B) nor plasma fibronectin (FIG. 5C).

Finally, to examine the activity of HtrA1 on the wound healing process, an external incised wound (~30 mm$^2$) was made from the tail skin of BALB/c mice. The excised wound pieces were incubated with 50 mM Tris-HCl control or each thrombolytic enzyme (2 mg/ml) at 37° C. for 72 hours. Wound healing was determined by observing the liquid containing the wound pieces and measuring the absorbance at 550 nm. In this in vivo wound tissue experiment using animals, treatment with the conventional thrombolytic enzyme resulted in continued bleeding due to the interruption of wound healing process while normal wound healing occurred in the treatment group of HtrA1 or HtrA2 (Table 2).

TABLE 2

| Groups | A550 |
| --- | --- |
| Control | $0.235 \pm 0.031$ |
| Streptokinase | $0.471 \pm 0.018^a$ |
| Urokinase | $0.404 \pm 0.037^a$ |
| HtrA1 | $0.203 \pm 0.028^{a,b}$ |
| HtrA2 | $0.247 \pm 0.033^{a,b}$ |

$^a$p < 0.05 significance difference from control group
$^b$p < 0.01 significance difference from Streptokinase group Example 1: Therapeutic Efficacy for Treatment of Thrombosis An animal experiment using a tail thrombosis model was performed to evaluate the thrombosis treatment efficacy of the thrombolytic agents of the present invention. A κ-carrageenan-induced tail thrombosis model was established in 15-week-old female BALB/c mice. Saline (control) or each thrombolytic enzyme was intraperitoneally injected into each group (n=8) of mice with tail thrombosis, and the length and proportion of the thrombosis site were measured 24 hours later, and the results are shown in Tables 3 and 4.

TABLE 3

| Groups | Dose (mg/kg) | Tail Length (cm) | Thrombosis Length (cm) | Thrombosis Ratio (%) |
| --- | --- | --- | --- | --- |
| Control | — | $9.21 \pm 0.08$ | $9.07 \pm 0.11^a$ | $98.50 \pm 0.80^a$ |
| Plasmin | 40 | $9.02 \pm 0.07$ | $3.37 \pm 0.45^b$ | $37.39 \pm 5.10^b$ |
| Streptokinase | 40 | $9.10 \pm 0.10$ | $5.11 \pm 1.22^a$ | $56.16 \pm 13.4^a$ |
| Urokinase | 40 | $9.07 \pm 0.10$ | $4.27 \pm 0.60^a$ | $47.08 \pm 6.51^a$ |
| HtrA1 (10 mg/kg) | 10 | $9.18 \pm 0.16$ | $4.72 \pm 1.06$ | $51.33 \pm 10.9$ |
| HtrA1 (20 mg/kg) | 20 | $9.12 \pm 0.10$ | $3.41 \pm 0.57$ | $37.41 \pm 6.43$ |
| HtrA1 (40 mg/kg) | 40 | $9.17 \pm 0.12$ | $1.61 \pm 0.49$ | $17.56 \pm 5.47$ |

$^a$p < 0.001 significance difference from HtrA1 (40 mg/kg) group
$^b$p < 0.01 significance difference from HtrA1 (40 mg/kg) group As shown in Table 3, the length and frequency of thrombosis tails in the HtrA1-treated group were significantly reduced compared to the conventional thrombolytic enzyme-treated groups in the mouse tail thrombosis model. It was shown that the thrombolytic effect has increased in proportion to the dosage. This confirms that HtrA1 has a statistically significant level of thrombosis treatment efficacy compared to conventional thrombolytic enzymes.

TABLE 4

| Groups | Dose (mg/kg) | Tail Length (cm) | Thrombosis Length (cm) | Thrombosis Ratio (%) |
| --- | --- | --- | --- | --- |
| Control | — | $9.19 \pm 0.09$ | $9.03 \pm 0.14^a$ | $98.25 \pm 1.16^a$ |
| Plasmin | 40 | $9.03 \pm 0.06$ | $3.40 \pm 0.41^b$ | $37.65 \pm 4.62^b$ |
| Streptokinase | 40 | $9.09 \pm 0.09$ | $4.97 \pm 1.16^a$ | $54.66 \pm 12.7^a$ |
| tPA | 40 | $9.06 \pm 0.08$ | $3.49 \pm 0.53^b$ | $38.53 \pm 6.06^b$ |
| HtrA2 (10 mg/kg) | 10 | $9.15 \pm 0.12$ | $4.55 \pm 1.11$ | $49.62 \pm 11.5$ |
| HtrA2 (20 mg/kg) | 20 | $9.11 \pm 0.11$ | $4.01 \pm 0.83$ | $44.01 \pm 9.18$ |
| HtrA2 (40 mg/kg) | 40 | $9.14 \pm 0.08$ | $2.19 \pm 0.75$ | $23.93 \pm 8.20$ |

$^a$p < 0.001 significance difference from HtrA2 (40 mg/kg) group
$^b$p < 0.01 significance difference from HtrA2 (40 mg/kg) group As shown in Table 4, the length and frequency of thrombosis tails in the HtrA2-treated group were also significantly reduced compared to the conventional thrombolytic enzyme-treated groups in the mouse tail thrombosis model. It was shown that the thrombolytic effect has increased in proportion to the dosage. This confirms that HtrA2 has a statistically significant level of thrombosis treatment efficacy compared to conventional thrombolytic enzymes.

Figure 7:
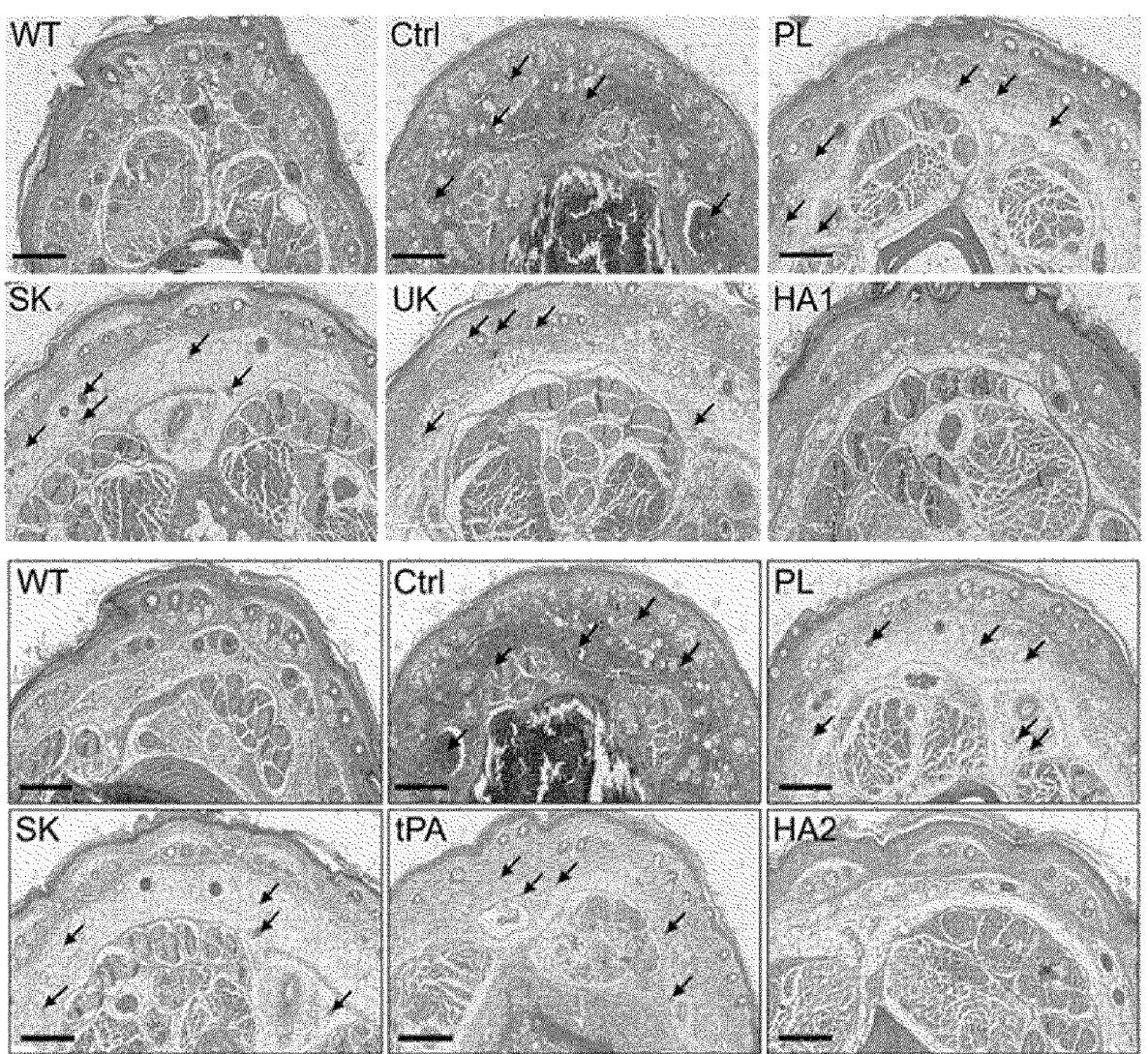
FIG. 7 is an H&E staining image result of thrombotic tail tissue confirming the therapeutic efficacy of the 'intravascular thrombolytic' polypeptide of the present invention on thrombosis in tail thrombosis mice using an animal model according to Example 1 of the present invention (Ctrl: control, PL: Plasmin, SK: streptokinase, UK: urokinase, tPA: tissue plasminogen activator, HA1: Polypeptide HtrA1 that recognizes 'intravascular thrombus' and dissolves thrombus, HA2: Polypeptide HtrA2 that recognizes 'intravascular thrombus' and dissolves thrombus).

In FIG. 7, observation of the thrombosis tail tissue after H&E staining, revealed the thrombotic mass and the thrombus dissolution in the samples from the group treated with conventional thrombolytic enzymes while there was no thrombotic mass in the HtrA1 and HtrA2 treatment groups, confirming excellent thrombolytic efficacy of HtrA1 and HtrA2.

Example 2: Therapeutic Efficacy for Treatment of Pulmonary Thromboembolism

Next, an animal experiment using a pulmonary thromboembolism model was performed to evaluate the prevention and treatment efficacy of thromboembolism. A model of pulmonary thromboembolism induced by adenosine 5'-diphosphate (ADP) was established in 15-week-old female C57BL/6 mice. Each group (n=8) of pulmonary thromboembolism mice fasted for 12 hours or longer, and then saline (control) or thrombolytic enzyme was injected intravenously at a dose of 40 mg/kg. After 30 minutes, ADP (150 mg/kg)

was injected into the mice to induce pulmonary thrombo-embolism, and then death was confirmed, and the results are shown in Tables 5 and 6.

TABLE 5

| Groups | Dose (mg/kg) | Lethal number/total | Protection rate (%) |
|---|---|---|---|
| Control | — | 6/6 | 0 |
| Plasmin | 40 | 3/6 | 50 |
| Streptokinase | 40 | 4/6 | 33 |
| Urokinase | 40 | 2/6 | 67 |
| HtrA1 | 40 | 0/6 | 100 |

From Table 5, in the lung thromboembolism mouse model, the survival rates of the plasmin, streptokinase, and urokinase treatment groups were 50%, 33%, and 66%, respectively, but the survival rate of the HtrA1 treatment group was 100%. This confirms that HtrA1 in the present invention has the perfect therapeutic and preventive effect on fatal pulmonary thromboembolism.

TABLE 6

| Groups | Dose (mg/kg) | Lethal number/total | Protection rate (%) |
|---|---|---|---|
| Control | — | 5/5 | 0 |
| Plasmin | 40 | 2/5 | 60 |
| Streptokinase | 40 | 4/5 | 20 |
| tPA | 40 | 3/5 | 40 |
| HtrA2 | 40 | 0/5 | 100 |

From Table 6, in the pulmonary thromboembolism mouse model, the survival rates of the plasmin, streptokinase, and tPA treatment groups were 60%, 20%, and 40%, respectively, but the survival rate of the HtrA2 treatment group was 100%. This also confirms that HtrA2 has a perfect thera-peutic and preventive effect on pulmonary thromboembo-lism.

Example 3: Effect on Removing the Risk of Internal Bleeding

A tail bleeding test was performed using 15-week-old C57BL/6 female mice to determine whether there is a risk of internal bleeding during the wound healing process when the thrombolytic protein HtrA1 is administered. Saline (control) or each thrombolytic enzyme was intravenously injected into a group of mice (n=5) at a dose of 40 mg/kg. After 30 minutes, the tail was cut from the anesthetized mouse, and the bleeding time and amount of blood were recorded while collecting blood until the bleeding stopped, and the hemo-globin content of the collected blood was measured. In addition, the time required for blood to clot in the severed tail vein of the rat was recorded.

Figure 8:
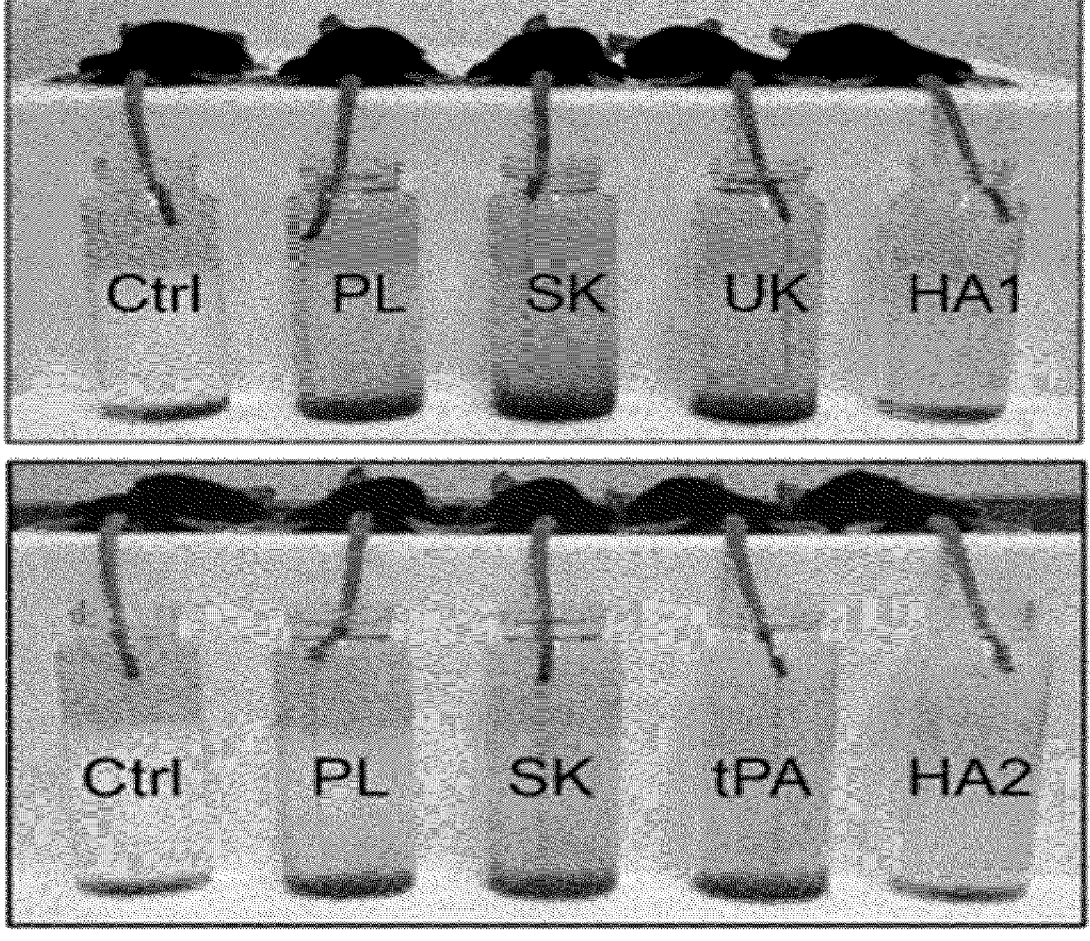
FIG. 8 is a bleeding image result confirming the effect of the 'intravascular thrombolytic' polypeptide of the present invention on wound healing using a wound animal model according to Example 3 of the present invention (Ctrl: control, PL: Plasmin, SK: streptokinase, UK: urokinase, tPA: tissue plasminogen activator, HA1: Polypeptide HtrA1 that recognizes 'intravascular thrombus' and dissolves thrombus, HA2: Polypeptide HtrA2 that recognizes 'intravascular thrombus' and dissolves thrombus).

As shown in FIG. 8, it was confirmed that the bleeding of HtrA1 and HtrA2 was significantly less than that of other thrombolytic enzymes in the mouse tail bleeding experi-ment. In the case of the HtrA1-treated group, the actual bleeding time (FIG. 9A), the amount of bleeding (FIG. 9B), the amount of hemoglobin lost (FIG. 9C), and the time taken to hemostasis (FIG. 9D) were measured. It was confirmed that the bleeding side effect was reduced to a level similar to that of the control group, being incomparably different from those of the conventional thrombolytic enzymes.

In the case of the HtrA2-treated group, the bleeding time (FIG. 10A), the amount of bleeding (FIG. 10B), the amount of hemoglobin lost (FIG. 10C), and the time taken to hemostasis (FIG. 10D) were measured. It was confirmed that the bleeding side effects were reduced to the level as much as that of the control group, being incomparably different from those of the conventional thrombolytic enzymes. HtrA1 and HtrA2 do not interfere with the hemostasis process, which is a part of the wound healing process, and thus completely reduce the risk of bleeding.

COMMERCIAL USE POTENTIAL

According to the present invention, the polypeptide for dissolving thrombus by recognizing 'intravascular throm-bus' dissolves thrombus in the blood of a mammal without serious bleeding side effects and has a preventive and therapeutic effect on thrombosis, thus preventing thrombosis and related diseases or it can be widely used as a therapeutic agent.

25

26

The invention claimed is:

1. A pharmaceutical composition for treating thrombosis, comprising a recombinant polypeptide consisting of amino acid residues 157 to 480 of the amino acid sequence set forth in SEQ ID NO: 9.

\*   \*   \*   \*   \*

SEQUENCE LISTING

```
<160> NUMBER OF SEQ ID NOS: 14

<210> SEQ ID NO 1
<211> LENGTH: 161
<212> TYPE: PRT
<213> ORGANISM: Artificial Sequence
<220> FEATURE:
<223> OTHER INFORMATION: amino acid sequence of thrombolytic domain of
      HtrA1 (HtrA1 as1)

<400> SEQUENCE: 1

Gly Ser Gly Phe Ile Val Ser Glu Asp Gly Leu Ile Val Thr Asn Ala
1               5                   10                  15

His Val Val Thr Asn Lys His Arg Val Lys Val Glu Leu Lys Asn Gly
            20                  25                  30

Ala Thr Tyr Glu Ala Lys Ile Lys Asp Val Asp Glu Lys Ala Asp Ile
        35                  40                  45

Ala Leu Ile Lys Ile Asp His Gln Gly Lys Leu Pro Val Leu Leu Leu
    50                  55                  60
```

-continued

```
Gly Arg Ser Ser Glu Leu Arg Pro Gly Glu Phe Val Val Ala Ile Gly
65                  70                  75                  80

Ser Pro Phe Ser Leu Gln Asn Thr Val Thr Thr Gly Ile Val Ser Thr
                85                  90                  95

Thr Gln Arg Gly Gly Lys Glu Leu Gly Leu Arg Asn Ser Asp Met Asp
            100                 105                 110

Tyr Ile Gln Thr Asp Ala Ile Ile Asn Tyr Gly Asn Ser Gly Gly Pro
        115                 120                 125

Leu Val Asn Leu Asp Gly Glu Val Ile Gly Ile Asn Thr Leu Lys Val
    130                 135                 140

Thr Ala Gly Ile Ser Phe Ala Ile Pro Ser Asp Lys Ile Lys Lys Phe
145                 150                 155                 160

Leu

<210> SEQ ID NO 2
<211> LENGTH: 177
<212> TYPE: PRT
<213> ORGANISM: Artificial Sequence
<220> FEATURE:
<223> OTHER INFORMATION: amino acid sequence of thrombolytic domain of
      HtrA2 (HtrA2 as1)

<400> SEQUENCE: 2

Ile Leu Asp Arg His Pro Phe Leu Gly Arg Glu Val Pro Ile Ser Asn
1               5                   10                  15

Gly Ser Gly Phe Val Val Ala Ala Asp Gly Leu Ile Val Thr Asn Ala
                20                  25                  30

His Val Val Ala Asp Arg Arg Arg Val Arg Val Arg Leu Leu Ser Gly
        35                  40                  45

Asp Thr Tyr Glu Ala Val Val Thr Ala Val Asp Pro Val Ala Asp Ile
    50                  55                  60

Ala Thr Leu Arg Ile Gln Thr Lys Glu Pro Leu Pro Thr Leu Pro Leu
65                  70                  75                  80

Gly Arg Ser Ala Asp Val Arg Gln Gly Glu Phe Val Val Ala Met Gly
                85                  90                  95

Ser Pro Phe Ala Leu Gln Asn Thr Ile Thr Ser Gly Ile Val Ser Ser
            100                 105                 110

Ala Gln Arg Pro Ala Arg Asp Leu Gly Leu Pro Gln Thr Asn Val Glu
        115                 120                 125

Tyr Ile Gln Thr Asp Ala Ala Ile Asp Phe Gly Asn Ser Gly Gly Pro
    130                 135                 140

Leu Val Asn Leu Asp Gly Glu Val Ile Gly Val Asn Thr Met Lys Val
145                 150                 155                 160

Thr Ala Gly Ile Ser Phe Ala Ile Pro Ser Asp Arg Leu Arg Glu Phe
                165                 170                 175

Leu

<210> SEQ ID NO 3
<211> LENGTH: 103
<212> TYPE: PRT
<213> ORGANISM: Artificial Sequence
<220> FEATURE:
<223> OTHER INFORMATION: amino acid sequence of thrombus cognitive
      domain of HtrA1 (HtrA1 as2)

<400> SEQUENCE: 3

Thr Glu Ser His Asp Arg Gln Ala Lys Gly Lys Ala Ile Thr Lys Lys
```

```
1               5                    10                   15

Lys Tyr Ile Gly Ile Arg Met Met Ser Leu Thr Ser Ser Lys Ala Lys
                20                  25                  30

Glu Leu Lys Asp Arg His Arg Asp Phe Pro Asp Val Ile Ser Gly Ala
            35                  40                  45

Tyr Ile Ile Glu Val Ile Pro Asp Thr Pro Ala Glu Ala Gly Gly Leu
        50                  55                  60

Lys Glu Asn Asp Val Ile Ile Ser Ile Asn Gly Gln Ser Val Val Ser
65                  70                  75                  80

Ala Asn Asp Val Ser Asp Val Ile Lys Arg Glu Ser Thr Leu Asn Met
                85                  90                  95

Val Val Arg Arg Gly Asn Glu
            100
```

```
<210> SEQ ID NO 4
<211> LENGTH: 82
<212> TYPE: PRT
<213> ORGANISM: Artificial Sequence
<220> FEATURE:
<223> OTHER INFORMATION: amino acid sequence of thrombus cognitive
      domain of HtrA2 (HtrA2 as2)

<400> SEQUENCE: 4

Val Met Met Leu Thr Leu Ser Pro Ser Ile Leu Ala Glu Leu Gln Leu
1               5                    10                   15

Arg Glu Pro Ser Phe Pro Asp Val Gln His Gly Val Leu Ile His Lys
                20                  25                  30

Val Ile Leu Gly Ser Pro Ala His Arg Ala Gly Leu Arg Pro Gly Asp
            35                  40                  45

Val Ile Leu Ala Ile Gly Glu Gln Met Val Gln Asn Ala Glu Asp Val
        50                  55                  60

Tyr Glu Ala Val Arg Thr Gln Ser Gln Leu Ala Val Gln Ile Arg Arg
65                  70                  75                  80

Gly Arg
```

```
<210> SEQ ID NO 5
<211> LENGTH: 483
<212> TYPE: DNA
<213> ORGANISM: Artificial Sequence
<220> FEATURE:
<223> OTHER INFORMATION: base sequence of thrombolytic domain of HtrA1
      (HtrA1 bs1)

<400> SEQUENCE: 5
gggtctgggt ttattgtgtc ggaagatgga ctgatcgtga caaatgccca cgtggtgacc        60
aacaagcacc gggtcaaagt tgagctgaag aacggtgcca cttacgaagc caaaatcaag       120
gatgtggatg agaaagcaga catcgcactc atcaaaattg accaccaggg caagctgcct       180
gtcctgctgc ttggccgctc ctcagagctg cggccgggag agttcgtggt cgccatcgga       240
agcccgtttt cccttcaaaa cacagtcacc accgggatcg tgagcaccac ccagcgaggc       300
ggcaaagagc tggggctccg caactcagac atggactaca tccagaccga cgccatcatc       360
aactatggaa actcgggagg cccgttagta aacctggacg gtgaagtgat tggaattaac       420
actttgaaag tgacagctgg aatctccttt gcaatcccat ctgataagat taaaaagttc       480
ctc                                                                      483
```

```
<210> SEQ ID NO 6
```

```
<211> LENGTH: 531
<212> TYPE: DNA
<213> ORGANISM: Artificial Sequence
<220> FEATURE:
<223> OTHER INFORMATION: base sequence of thrombolytic domain of HtrA2
      (HtrA2 bs1)

<400> SEQUENCE: 6
atcctggacc ggcacccttt cttgggccgc gaggtcccta tctcgaacgg ctcaggattc      60
gtggtggctg ccgatgggct cattgtcacc aacgcccatg tggtggctga tcggcgcaga     120
gtccgtgtga gactgctaag cggcgacacg tatgaggccg tggtcacagc tgtggatccc     180
gtggcagaca tcgcaacgct gaggattcag actaaggagc tctctcccac gctgcctctg     240
ggacgctcag ctgatgtccg gcaaggggag tttgttgttg ccatgggaag tccctttgca     300
ctgcagaaca cgatcacatc cggcattgtt agctctgctc agcgtccagc cagagacctg     360
ggactccccc aaaccaatgt ggaatacatt caaactgatg cagctattga ttttggaaac     420
tctggaggtc ccctggttaa cctggatggg gaggtgattg gagtgaacac catgaaggtc     480
acagctggaa tctcctttgc catcccttct gatcgtcttc gagagtttct g              531

<210> SEQ ID NO 7
<211> LENGTH: 309
<212> TYPE: DNA
<213> ORGANISM: Artificial Sequence
<220> FEATURE:
<223> OTHER INFORMATION: base sequence of thrombus cognitive domain of
      HtrA1 (HtrA1 bs2)

<400> SEQUENCE: 7
acggagtccc atgaccgaca ggccaaagga aaagccatca ccaagaagaa gtatattggt      60
atccgaatga tgtcactcac gtccagcaaa gccaaagagc tgaaggaccg gcaccgggac     120
ttcccagacg tgatctcagg agcgtatata attgaagtaa ttcctgatac cccagcagaa     180
gctggtggtc tcaaggaaaa cgacgtcata atcagcatca atggacagtc cgtggtctcc     240
gccaatgatg tcagcgacgt cattaaaagg gaaagcaccc tgaacatggt ggtccgcagg     300
ggtaatgaa                                                               309

<210> SEQ ID NO 8
<211> LENGTH: 246
<212> TYPE: DNA
<213> ORGANISM: Artificial Sequence
<220> FEATURE:
<223> OTHER INFORMATION: base sequence of thrombus cognitive domain of
      HtrA2 (HtrA2 bs2)

<400> SEQUENCE: 8
gtgatgatgc tgaccctgag tcccagcatc cttgctgaac tacagcttcg agaaccaagc      60
tttcccgatg ttcagcatgg tgtactcatc cataaagtca tcctgggctc ccctgcacac     120
cgggctggtc tgcggcctgg tgatgtgatt ttggccattg gggagcagat ggtacaaaat     180
gctgaagatg tttatgaagc tgttcgaacc caatcccagt tggcagtgca gatccggcgg     240
ggacga                                                                  246

<210> SEQ ID NO 9
<211> LENGTH: 480
<212> TYPE: PRT
<213> ORGANISM: Artificial Sequence
<220> FEATURE:
<223> OTHER INFORMATION: amino acid sequence of HtrA1 (HtrA1)
```

-continued

<400> SEQUENCE: 9

Met Gln Ile Pro Arg Ala Ala Leu Leu Pro Leu Leu Leu Leu Leu Leu
1               5                   10                  15

Ala Ala Pro Ala Ser Ala Gln Leu Ser Arg Ala Gly Arg Ser Ala Pro
            20                  25                  30

Leu Ala Ala Gly Cys Pro Asp Arg Cys Glu Pro Ala Arg Cys Pro Pro
        35                  40                  45

Gln Pro Glu His Cys Glu Gly Gly Arg Ala Arg Asp Ala Cys Gly Cys
    50                  55                  60

Cys Glu Val Cys Gly Ala Pro Glu Gly Ala Ala Cys Gly Leu Gln Glu
65                  70                  75                  80

Gly Pro Cys Gly Glu Gly Leu Gln Cys Val Val Pro Phe Gly Val Pro
                85                  90                  95

Ala Ser Ala Thr Val Arg Arg Arg Ala Gln Ala Gly Leu Cys Val Cys
            100                 105                 110

Ala Ser Ser Glu Pro Val Cys Gly Ser Asp Ala Asn Thr Tyr Ala Asn
            115                 120                 125

Leu Cys Gln Leu Arg Ala Ala Ser Arg Arg Ser Glu Arg Leu His Arg
    130                 135                 140

Pro Pro Val Ile Val Leu Gln Arg Gly Ala Cys Gly Gln Gly Gln Glu
145                 150                 155                 160

Asp Pro Asn Ser Leu Arg His Lys Tyr Asn Phe Ile Ala Asp Val Val
                165                 170                 175

Glu Lys Ile Ala Pro Ala Val Val His Ile Glu Leu Phe Arg Lys Leu
            180                 185                 190

Pro Phe Ser Lys Arg Glu Val Pro Val Ala Ser Gly Ser Gly Phe Ile
            195                 200                 205

Val Ser Glu Asp Gly Leu Ile Val Thr Asn Ala His Val Val Thr Asn
    210                 215                 220

Lys His Arg Val Lys Val Glu Leu Lys Asn Gly Ala Thr Tyr Glu Ala
225                 230                 235                 240

Lys Ile Lys Asp Val Asp Glu Lys Ala Asp Ile Ala Leu Ile Lys Ile
                245                 250                 255

Asp His Gln Gly Lys Leu Pro Val Leu Leu Leu Gly Arg Ser Ser Glu
                260                 265                 270

Leu Arg Pro Gly Glu Phe Val Val Ala Ile Gly Ser Pro Phe Ser Leu
            275                 280                 285

Gln Asn Thr Val Thr Thr Gly Ile Val Ser Thr Thr Gln Arg Gly Gly
    290                 295                 300

Lys Glu Leu Gly Leu Arg Asn Ser Asp Met Asp Tyr Ile Gln Thr Asp
305                 310                 315                 320

Ala Ile Ile Asn Tyr Gly Asn Ser Gly Gly Pro Leu Val Asn Leu Asp
                325                 330                 335

Gly Glu Val Ile Gly Ile Asn Thr Leu Lys Val Thr Ala Gly Ile Ser
            340                 345                 350

Phe Ala Ile Pro Ser Asp Lys Ile Lys Lys Phe Leu Thr Glu Ser His
            355                 360                 365

Asp Arg Gln Ala Lys Gly Lys Ala Ile Thr Lys Lys Lys Tyr Ile Gly
    370                 375                 380

Ile Arg Met Met Ser Leu Thr Ser Ser Lys Ala Lys Glu Leu Lys Asp
385                 390                 395                 400

Arg His Arg Asp Phe Pro Asp Val Ile Ser Gly Ala Tyr Ile Ile Glu
                405                 410                 415

-continued

```
Val Ile Pro Asp Thr Pro Ala Glu Ala Gly Gly Leu Lys Glu Asn Asp
          420                 425                 430

Val Ile Ile Ser Ile Asn Gly Gln Ser Val Val Ser Ala Asn Asp Val
          435                 440                 445

Ser Asp Val Ile Lys Arg Glu Ser Thr Leu Asn Met Val Val Arg Arg
          450                 455                 460

Gly Asn Glu Asp Ile Met Ile Thr Val Ile Pro Glu Glu Ile Asp Pro
465                 470                 475                 480

<210> SEQ ID NO 10
<211> LENGTH: 458
<212> TYPE: PRT
<213> ORGANISM: Artificial Sequence
<220> FEATURE:
<223> OTHER INFORMATION: amino acid sequence of HtrA2 (HtrA2)

<400> SEQUENCE: 10

Met Ala Ala Pro Arg Ala Gly Arg Gly Ala Gly Trp Ser Leu Arg Ala
1                 5                  10                  15

Trp Arg Ala Leu Gly Gly Ile Arg Trp Gly Arg Arg Pro Arg Leu Thr
          20                 25                 30

Pro Asp Leu Arg Ala Leu Leu Thr Ser Gly Thr Ser Asp Pro Arg Ala
          35                 40                 45

Arg Val Thr Tyr Gly Thr Pro Ser Leu Trp Ala Arg Leu Ser Val Gly
          50                 55                 60

Val Thr Glu Pro Arg Ala Cys Leu Thr Ser Gly Thr Pro Gly Pro Arg
65                 70                 75                 80

Ala Gln Leu Thr Ala Val Thr Pro Asp Thr Arg Thr Arg Glu Ala Ser
          85                 90                 95

Glu Asn Ser Gly Thr Arg Ser Arg Ala Trp Leu Ala Val Ala Leu Gly
          100                105                110

Ala Gly Gly Ala Val Leu Leu Leu Trp Gly Gly Gly Arg Gly Pro
          115                120                125

Pro Ala Val Leu Ala Ala Val Pro Ser Pro Pro Ala Ser Pro Arg
          130                135                140

Ser Gln Tyr Asn Phe Ile Ala Asp Val Val Glu Lys Thr Ala Pro Ala
145                150                155                160

Val Val Tyr Ile Glu Ile Leu Asp Arg His Pro Phe Leu Gly Arg Glu
          165                170                175

Val Pro Ile Ser Asn Gly Ser Gly Phe Val Val Ala Ala Asp Gly Leu
          180                185                190

Ile Val Thr Asn Ala His Val Val Ala Asp Arg Arg Arg Val Arg Val
          195                200                205

Arg Leu Leu Ser Gly Asp Thr Tyr Glu Ala Val Val Thr Ala Val Asp
          210                215                220

Pro Val Ala Asp Ile Ala Thr Leu Arg Ile Gln Thr Lys Glu Pro Leu
225                230                235                240

Pro Thr Leu Pro Leu Gly Arg Ser Ala Asp Val Arg Gln Gly Glu Phe
          245                250                255

Val Val Ala Met Gly Ser Pro Phe Ala Leu Gln Asn Thr Ile Thr Ser
          260                265                270

Gly Ile Val Ser Ser Ala Gln Arg Pro Ala Arg Asp Leu Gly Leu Pro
          275                280                285

Gln Thr Asn Val Glu Tyr Ile Gln Thr Asp Ala Ala Ile Asp Phe Gly
          290                295                300
```

```
Asn Ser Gly Gly Pro Leu Val Asn Leu Asp Gly Glu Val Ile Gly Val
305             310             315             320

Asn Thr Met Lys Val Thr Ala Gly Ile Ser Phe Ala Ile Pro Ser Asp
            325             330             335

Arg Leu Arg Glu Phe Leu His Arg Gly Glu Lys Lys Asn Ser Ser Ser
        340             345             350

Gly Ile Ser Gly Ser Gln Arg Arg Tyr Ile Gly Val Met Met Leu Thr
        355             360             365

Leu Ser Pro Ser Ile Leu Ala Glu Leu Gln Leu Arg Glu Pro Ser Phe
        370             375             380

Pro Asp Val Gln His Gly Val Leu Ile His Lys Val Ile Leu Gly Ser
385             390             395             400

Pro Ala His Arg Ala Gly Leu Arg Pro Gly Asp Val Ile Leu Ala Ile
            405             410             415

Gly Glu Gln Met Val Gln Asn Ala Glu Asp Val Tyr Glu Ala Val Arg
            420             425             430

Thr Gln Ser Gln Leu Ala Val Gln Ile Arg Arg Gly Arg Glu Thr Leu
        435             440             445

Thr Leu Tyr Val Thr Pro Glu Val Thr Glu
    450             455
```

```
<210> SEQ ID NO 11
<211> LENGTH: 29
<212> TYPE: DNA
<213> ORGANISM: Artificial Sequence
<220> FEATURE:
<223> OTHER INFORMATION: HtrA1 forward primer

<400> SEQUENCE: 11
aattcatatg caagggcagg aagatccca                                   29

<210> SEQ ID NO 12
<211> LENGTH: 30
<212> TYPE: DNA
<213> ORGANISM: Artificial Sequence
<220> FEATURE:
<223> OTHER INFORMATION: HtrA1 reverse primer

<400> SEQUENCE: 12
tatctcgagc tatgggtcaa tttcttcggg                                  30

<210> SEQ ID NO 13
<211> LENGTH: 28
<212> TYPE: DNA
<213> ORGANISM: Artificial Sequence
<220> FEATURE:
<223> OTHER INFORMATION: HtrA2 forward primer

<400> SEQUENCE: 13
gtcctcgccc atatggccgt ccctagcc                                    28

<210> SEQ ID NO 14
<211> LENGTH: 29
<212> TYPE: DNA
<213> ORGANISM: Artificial Sequence
<220> FEATURE:
<223> OTHER INFORMATION: HtrA2 reverse primer

<400> SEQUENCE: 14
ggctctcgag tcattctgtg acctcaggg                                   29
```